United States Patent [19]

Malen et al.

[11] Patent Number: 4,459,306

[45] Date of Patent: Jul. 10, 1984

[54] TRICYCLIC ETHERS, THEIR PROCESS OF PREPARATION AND THEIR USE AS MEDICINES

[75] Inventors: Charles Malen, Fresnes; Jean-Claude Poignant, Bures S/Yvette, both of France

[73] Assignee: Science Union et Cie, Suresnes, France

[21] Appl. No.: 251,052

[22] Filed: Apr. 6, 1981

[30] Foreign Application Priority Data

Apr. 10, 1980 [FR] France ............................... 80 08023

[51] Int. Cl.³ ................. C07D 321/10; C07D 327/02; A61K 31/335; A61K 31/39
[52] U.S. Cl. ............................ 424/276; 260/465 F; 260/544 D; 424/278; 424/282; 424/267; 424/274; 544/375; 544/378; 544/377; 546/203; 546/204; 549/10; 549/348; 549/349; 562/432; 562/471; 562/472
[58] Field of Search ...................... 549/349, 348, 10; 424/276, 278, 282

[56] References Cited

U.S. PATENT DOCUMENTS

| | | | |
|---|---|---|---|
| 3,758,528 | 9/1973 | Malen et al. | 260/239 D |
| 3,821,249 | 6/1974 | Malen et al. | 260/330 |
| 4,335,122 | 1/1982 | McFadden et al. | 549/349 X |

FOREIGN PATENT DOCUMENTS

| | | |
|---|---|---|
| 1312891 | 11/1962 | France . |
| 1312889 | 11/1962 | France . |
| 1827 | 5/1963 | France . |
| 2315272 | 1/1977 | France . |

*Primary Examiner*—Joseph Paul Brust
*Attorney, Agent, or Firm*—Gordon W. Hueschen

[57] ABSTRACT

This invention relates to novel tricyclic ethers, pharmaceutically acceptable addition salts and optical isomers therefrom. The compounds described herein are useful as psychotropic agents in the treatment of depression and anxiety. Also included herein are methods of preparing said compounds, pharmaceutical compositions including them and methods of treating human or animal beings by administering these pharmaceutical compositions.

22 Claims, No Drawings

TRICYCLIC ETHERS, THEIR PROCESS OF PREPARATION AND THEIR USE AS MEDICINES

PRIOR ART

The prior art may be illustrated by the U.S. Pat. No. 3,758,528 to Ch. Malen et al. and U.S. Pat. No. 3,821,249.

SUMMARY OF THE INVENTION

The invention provides new aminoalkyl substituted 11H-dibenzooxepines, processes for preparing them, pharmaceutical compositions comprising them and methods of treating certain central nervous system disturbances by the same.

This invention relates to novel tricyclic ethers, their processes of preparation and to pharmaceutical compositions containing them.

More precisely the present invention provides 11H-dibenzooxepines substituted by an aminoalkyl chain and having the following general formula:

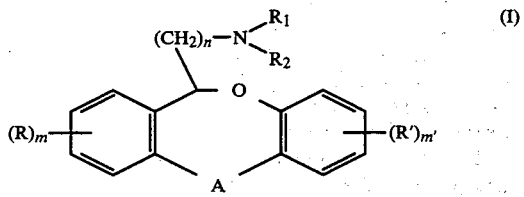

wherein R and R', the same or different, are a hydrogen or a halogen atom, a lower alkyl radical up to 5 carbon atoms, a lower alkoxy radical up to 5 carbon atoms, a trifluoromethyl, a trifluoromethoxy, a trifluoromethylthio, an alkylenedioxy or an alkylthio radical, A represents an oxygen or a sulphur atom, a sulphoxide or a sulphonyl radical, $R_1$ and $R_2$, the same or different, represent a hydrogen atom, a lower alkyl radical up to 5 carbon atoms, a lower aralkyl radical, a lower hydroxyalkyl radical or may form together an alkylene chain of 3 to 6 carbon atoms which may be interrupted by one or two heteroatoms, optionally substituted by a lower alkyl radical, n represents an integer of 2 to 4 m and m', the same or different, are integers of 1 or 2.

The invention provides also addition salts of compounds of general formula I with mineral or organic acids, preferably with therapeutically compatible acids. However other acids may be used for identification, separation, purification or splitting purposes.

Compounds of general formula I possess one or more asymetric carbon atoms and may thus split into optical isomers. Their forms dextro- or laevorotatory are included in the present invention as well as the racemic form.

As acids, which may be added to the compounds of general formula I, there may be cited as examples, hydrochloric acid, hydrobromic acid, phosphoric acid, sulphuric acid, formic acid, acetic acid, lactic acid, pyruvic acid, succinic acid, citric acid, tartaric acid, fumaric acid, maleic acid, benzoic acid, salicylic acid, methane sulphonic acid, isethionic acid, benzenesulphonic acid, etc.

The compounds of general formula I and their salts possess interesting pharmaceutical properties, more especially psychotropic properties. They have on the central nervous system antidepressant, sedative and anxiolytic activity. In animals they decrease the muscle tone, inhibit aggressivity, convulsions, catatonia and hypothermia.

On the other hand they are antagonists of the ptosis of eyelid provoked by tetrabenazine and they increase stereotypic movements provoked by amphetamine.

They are active by oral route as well as by parenteral route.

They may be used in human or in veterinary medicine as antidepressant, sedative or anxiolytic medicines.

The invention provides also pharmaceutical compositions, including at least one compound of general formula I or a therapeutically compatible acid addition salt thereof as active principle in admixture or conjunction with one or more pharmaceutically suitable vehicles or carriers.

Among the pharmaceutical compositions of the invention there may be cited those suitable for parenteral, oral, rectal or sublingual administration such as tablets, capsules, solutions or suppositories.

The doses to be administered vary depending on the weight and age of the patient, the route of administration and the symptoms to be treated. Generally the unit dosage is from 0.5 to 10 mg and the daily dose from 0.5 to 30 mg in men.

The invention further includes a method for treating central nervous system disorders such as depression, anxiety or irritation, which consists in administering to such patients an effective amount of a compound of general formula I or a salt thereof.

The invention provides also processes of preparing 11H-dibenzooxepines of general formula I, characterized by submitting a hydroxyphenyl A-benzoic acid of general formula II:

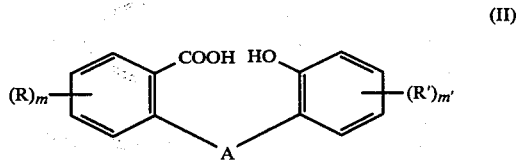

in which R, R', m and m' have the previously given meanings and

A is an oxygen or a sulphur atom, to the action of a dehydrating agent such as the acetic anhydride or to the action of thionyl chloride and the cyclization by a tertiary amine in order to obtain a 11H-dibenzooxepinone of general formula III:

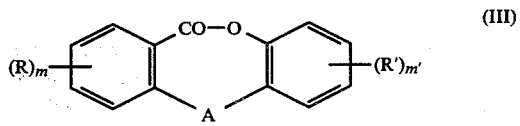

in which the meanings of R, R', A, m and m' are as above defined, which is selectively submitted to the action of an ylide of alkoxy carbonyl methyl phosphonium of general formula IV:

wherein

Ar represents a phenyl radical, optionally substituted and $R_4$ is a lower alkyl or aralkyl radical which may be substituted, in order to obtain the corresponding alkoxycarbonyl methylidene derivative of general formula V:

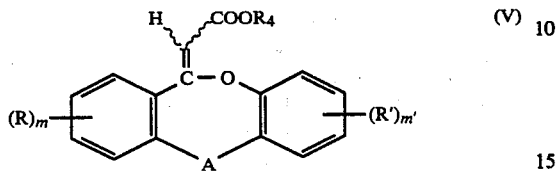

in which A, R, R', $R_4$, m and m' are as defined above, and submit it to the action of a hydrogenating agent in order to obtain an alkoxycarbonyl methylenic derivative of general formula VI:

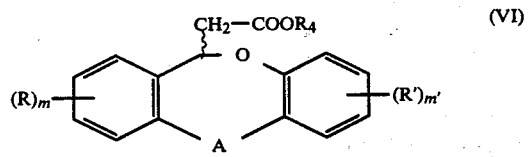

in which A, R, R', $R_4$, m and m' are the same as above, and which is reduced in the corresponding ethanol by a hydrogenating agent, particularly by a mixed hydride of an basic metal, to obtain a compound of general formula VII:

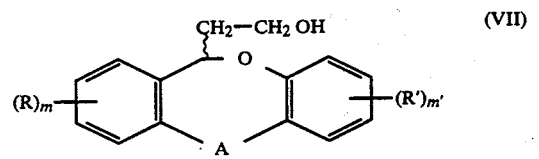

in which R, R', A, m and m' are as above defined and which is transformed by known processes in an ester of general formula VIII:

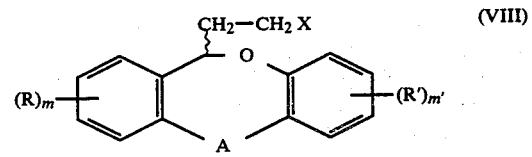

wherein

R, R', m, m' and A are as defined above and

X is Cl, Br, I, alkyl $SO_3$ or aryl $SO_3$ which is reacted with an amine derivative of general formula IX:

in which $R_1$ and $R_2$ stand as previously defined, to produce an ethylaminated derivative of general formula I, which is either subjected, when A represents a sulphur atom, to the action of an oxidizing agent in order to form the corresponding sulphoxide or sulphonyl derivative, or salified by the addition of a mineral or organic acid.

The invention provides further another process for preparing compounds of general formula I in which n=3 characterized by subjecting a compound of general formula VIII to the action of a metal of cyanide, the formula

Me—CN in which Me is an alkali or alkaline earth metal radical, in order to obtain a compound of general formula X:

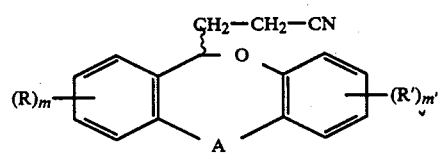

which is further reduced by a hydrogenating agent, such as a mixed hydride or is subjected to catalytic hydrogenation to obtain an amine of general formula I in which n is equal to 3 and which is either alkylated or aralkylated by an alkylating or aralkylating agent: in order to obtain the corresponding secondary or tertiary amine, or is resolved in optical isomers by a chiralic acid or is salified by the addition of a mineral or organic acid.

The invention includes also a process for preparing compounds of general formula I in which n=2, which consists in subjecting a dibenzo oxepinone of general formula III in which R, R', A, m and m' stand as previously defined, to the action of a cyanomethyl phosphoniumylide of general formula IV':

in which Ar is as previously defined in order to obtain the cyanomethylidenic derivative of general formula XI:

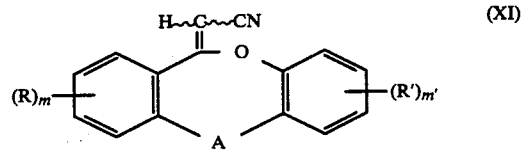

in which R, R', A, m and m' are defined previously, and which is selectively hydrogenated in the corresponding amino-ethylidenic derivative of general formula XII:

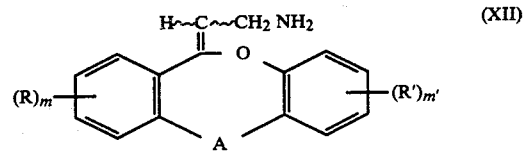

of form Z or E in which A, R, R', m and m' are as stated above and which is reduced by a hydrogenating agent such as a metal hydride or is subjected to catalytic hydrogenation to obtain an ethylaminated derivative of general formula I in which $R_1$ and $R_2$=H and n=2, and which may be either salified by addition of a mineral or organic acid, or resolved in optical isomers by a chilaric acid, or alkylated or aralkylated by a carbonylated derivative in presence of a reducing agent, or, when A is a sulphur atom, oxidized in a sulphoxide or a sulphonic derivative.

The invention further provides a process for preparing compounds of general formula I, which consists in subjecting an alkyloxycarbonylmethylidenic compound of general formula V to a sparing saponification in a basic medium to obtain a hydroxycarboxymethylidenic derivative of general formula XIV:

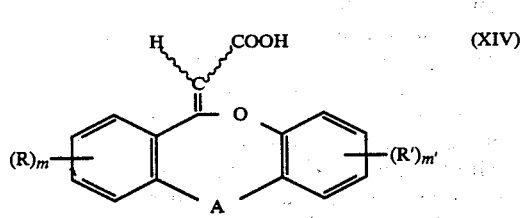

in which R, R', A, m and m' have the previously given meanings, in the form Z or E, which is condensed with an amine derivative of general formula IX wherein $R_1$ and $R_2$ are as stated above, in the presence of a functionalization agent for the carboxyl group, to obtain the corresponding methylidenic amide of general formula XV:

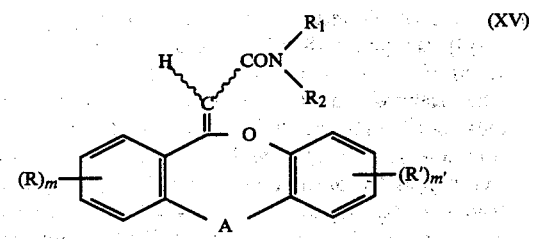

wherein $R_1$, $R_2$, R, A, m and m' are as previously defined, which may be reduced or hydrogenated in an ethylamine compound of general formula I in which n=2.

It is to be mentioned that starting material of formula III is obtained by known methods and that the intermediate of general formula XVI:

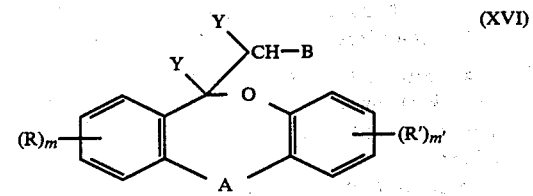

wherein A, R, R', m and m' are as previously defined and

Y is a hydrogen atom or together YY form a double bond

B is

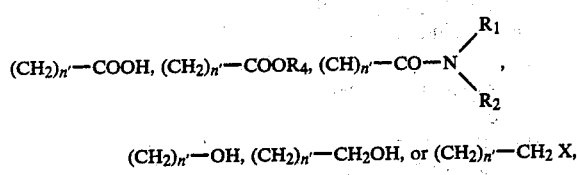

wherein $R_1$ and $R_2$ and n are as previously defined, $R_4$ is as defined in formula V, and X is as defined in formula VIII, and n' is 0 to 2, corresponding to the formula V, VI, VII, VIII, X, Xi, XII, XIV and XV, which are all new compounds and form part of the invention.

The following examples illustrate the invention, without limiting it.

EXAMPLE 1 dl N-diethyl 2-[11H-dibenzo (b,e)-1,4 dioxepin-11-yl] ethylamine and its fumarate

Step A 11H-dibenzo (b,e)-1,4-dioxepine-11-one 5.06 g of 2-(2-hydroxyphenoxy) benzoic acid were suspended in 35 ml of newly distilled acetic anhydride, then the mixture was refluxed for 3 hours while the reaction is controlled from time to time by analyzing a sample of the mixture by gas chromatography. The excess of acetic anhydride was then removed by distillation under reduced pressure and the oily residue crystallized at rest. The crystals were left overnight in a refrigerator; then they were taken up with some ml of ether. The crystalline mass was filtered off, squeezed out, rinsed with some ml of ether and dried under vacuum. The obtained dibenzo (b,e) dioxepinone was purified on fractional distillation under reduced pressure. The pure product distills over at 0.01 mmHg, and melts at 62°-66° C.

Step B 11-(methoxycarbonyl methylidene) [11H-dibenzo (b,e)-1,4-dioxepin]

15.90 g of 11H-dibenzo (b,e)-1,4-dioxepin-11-one were dissolved in 25 ml of toluene, then there were added 25 g of methoxy carbonyl methylene triphenyl phosphonium ylide. The mixture was refluxed for 15 hours, then cooled down and 2.5 g of phosphonium ylide were added. The mixture was refluxed again for 24 hours until the gas chromatography shows that no starting material remains. The heating was then stopped and the solvent was distilled under vacuum. The residue was taken up with anhydrous ether. There was formed a gummy mass which was left while the ether was filtered and then evaporated under vacuum. There were obtained 33 g of raw product which is a mixture of Z and E isomers.

The product was purified by chromatography on a column of silica, then eluted with a mixture of equal parts of benzene and chloroform. There were taken fractions of 50 ml. The earlier fractions were eliminated then a high A isomer grade fraction was taken off. After recrystallization from acetonitrile there were obtained 2.7 g of A isomer melting at 59°-60° C. From the bottom fractions there was isolated an oil which slowly crystallizes. By recrystallization from isopropylic ether, there were obtained 4 g of B isomer, melting at 81°-83° C.

Step C 11-(methoxycarbonyl methyl) [11H-dibenzo (b,e)-1,4-dioxepin]

27 g of 11-(methoxycarbonyl methylidene) dibenzo (b,e)-1,4-dioxepin (A or B isomer) were dissolved in 150 ml of methanol. The solution was purged with bubbling nitrogen, then 0.5 g of platinum dioxide were added. The mixture was hydrogenated under atmospheric pressure until the end of the absorption. The catalyst was filtered off and the methanol solution was half concentrated. The crystallization was started up, then the crystalline mixture was left at rest for 10 hours in a refrigerator. The crystalline mass was suctioned off and then dried under vacuum in a dessicator over phosphoric acid. There were obtained 13 g of a hydrogenated product (yield: 48%). The pure product, after recrystallization, melts at 72°–74° C.

The same reduction may be performed with an amalgam of aluminum.

The amalgam of aluminium, prepared starting from 50.3 g of aluminum and 2.7 g of mercuric chloride, was suspended in 680 ml of dry ether. A solution of 75 g of 11-(methoxycarbonyl methylidene) [11H-dibenzo (b,e)-1,4-dioxepin] (A or B isomer) in 50 ml of dry ether was then added. A solution of 23.5 ml of water dropped to the reactional mixture for 4 hours under stirring. The reactional mixture was spontaneously heated with slight reflux. After completion of addition of water, the organic phase was isolated, washed, dried and evaporated under vacuum. The dry residue was recrystallized from 100 ml of ethanol. There were obtained 38 g of pure product, M.P.: 72°–75° C. (M.K.) yield: 51%.

Step D 11-hydroxyethyl [11H-dibenzo (b,e)-1,4-dioxepin]

33.7 g of 11-(methoxycarbonyl methyl) [dibenzo (b,e)-1,4-dioxepin] were added to 50 ml of tetrahydrofuran. This clear solution was cooled between 0° and 10° C. and one N solution of lithium triethylborohydride in tetrahydrofuran was very slowly added. This reactive solution was added for about 6 hours while the stirring and cooling were maintained. The mixture was then left between 0° and −5° C., and the excess of the reactive solution was hydrolyzed with 100 ml of a 3N hydrochloric acid solution. The tetrahydrofuran was evaporated. The residual aqueous phase was extracted thrice with isopropyl ether. The organic solutions were joined together, washed with hydrochloric acid and then water. The solvent was distilled off and there were obtained 32.2 g of 11-hydroxyethyl dibenzo (b,e)-1,4-dioxepin. This product recrystallized from the tetrahydrofuran gives 19.6 g of pure product (yield: 65%). The hydroxy ethyl compound distills at 160°–163° C. under 0.1 mmHg M.P.=62°–64° C. (M.K.).

Step E 11-(p.tolylsulfonyloxyethyl) [11H-dibenzo (b,e)-1,4-dioxepin]

7.4 g of 11-hydroxyethyl compound were dissolved in 4.8 ml of pyridine and 20 ml of acetonitrile. There was progressively added a solution of 6.1 g of p.toluenesulfonyl chloride in 20 ml of acetonitrile, for about 30 minutes. The mixture was left under stirring at room temperature for 12 hours then the pyridine hydrochloride which is formed was filtered off. Acetonitrile was then evaporated from the filtrate and the residue was taken up with water and ether. The ether phase was separated, and washed with one N sulfuric acid solution until neutrality of the washings. The ether was dried over magnesium sulfate and then evaporated to dryness. There was obtained 11 g of an oily product which is purified by crystallization in 15 ml of isopropylic ether. The mixture was left at rest in a refrigerator for 24 hours, then the crystals were filtered off and dried under vacuum. There were obtained 8.7 g of 11-(p.toluenesulfonyloxyethyl) 11H-dibenzo (b,e)-1,4-dioxepin (yield: 73%). The pure product melts at 64°–68° C.

Step F

N-diethyl 2-[11H-dibenzo (b,e)-1,4-dioxepin-11-yl] ethylamine 13.2 g of 11-(p.toluenesulfonyloxyethyl) 11H-dibenzo (b,e)-1,4 dioxepin and 4 g of diethylamine were dissolved in 100 ml of acetonitrile. The solution was heated up to 90° C. and maintained at this temperature for one hour, then cooled down. The reactional mixture was poured onto a mixture of water and ice, whereafter the precipitate was extracted with methylene chloride. The organic phase was separated off, dried and evaporated under vacuum. The dry residue was suspended in 20 ml of ether and 15 ml of water. The mixture was alkalized with 15 ml of one N solution of sodium hydroxide, then vigorously stirred and the ether phase was separated off. The ether phase was acidified with hydrochloric acid and the aqueous phase was alkalized. The formed precipitate was exhausted with ether. The ether phase was washed with water, dried over sodium sulfate, filtered and dried off. There were obtained 9.67 g of N-diethyl 2-[11H-dibenzo (b,e)-1,4-dioxepin-11-yl] ethylamine.

Step G 1.2 g of N-diethyl [11H-dibenzo (b,e)-1,4-dioxepin-11-yl] ethylamine then 0.81 g of citric acid dissolved in 15 ml of hot ethanol were suspended in 5 ml of ethanol. The reactive products were mixed and the so-formed clear solution was half-concentrated. The crystallization was started up, and the solution was left at rest overnight at room temperature. The precipitate of citrate was then separated off, rinsed with 2 ml of ethanol and dried at 50° C. under vacuum. There were obtained 1.2 g of N-diethyl 2-[11H-dibenzo (b,e)-1,4-dioxepin-11-yl] ethylamine citrate, melting at 123°–127° C. This salt is insoluble in water. N-diethyl 2-[11H-dibenzo (b,e)-1,4-dioxepin-11-yl]ethylamine fumarate, M.P.: 146°–148° C. (isopropanol) was prepared according to the same process.

EXAMPLE 2

N-diethyl 2-[2-chloro 11H-dibenzo (b,e)-1,4-dioxepin-11-yl] ethylamine, and its fumarate According to the procedure given in Example 1, starting from 2-(2-hydroxyphenoxy)-5-chlorobenzoic acid, (M.P.: 120°–121° C.), there were successively obtained:

2-chloro 11H-dibenzo (b,e)-1,4-dioxepin-11-one, (M.P.: 155°–158° C. (with sublimation);

11-(methoxycarbonylmethylidene)[2-chloro 11H-dibenzo(b,e)-1,4-dioxepin] Z and E isomers, M.P.: 123°–126° C. and 102°–106° C.;

11-(methoxycarbonylmethyl) [2-chloro 11H-dibenzo (b,e)-1,4-dioxepin], which is an oily product;

11-hydroxyethyl[2-chloro 11H-dibenzo (b,e)-1,4-dioxepin], which is an oily product;

11-(p.toluenesulfonyloxyethyl) [2-chloro 11H-dibenzo (b,e)-1,4-dioxepin], M.P.: 100°–108° C. (yield: 50%); and N-diethyl 2-[2-chloro 11H-dibenzo (b,e)-1,4-dioxepin-11-yl] ethylamine, M.P.: 154°–158° C. (acetonitrile).

EXAMPLE 3

N-pentamethylene 2-[3-chloro 11H-dibenzo (b,e)-1,4-dioxepin-11-yl] ethylamine and its citrate According to the procedure given in Example 1, starting from (2-hydroxyphenoxy) 4-chlorobenzoic acid (M.P.: 177°–179° C.), there were successively obtained:

3-chloro 11H-dibenzo(b,e)-1,4-dioxepin-11-one, M.P.: 147°–149° C. (with sublimation);

11-(methoxycarbonylmethylidene) 3-chloro [11H-dibenzo (b,e)-1,4-dioxepin] Z or E isomer, melting at 97°–98° C. and 107°–110° C.;

11-(methoxycarbonylmethyl)-3-chloro [11H-dibenzo (b,e)-1,4-dioxepin], which is an oil;

11-hydroxyethyl 3-chloro [11H-dibenzo (b,e)-1,4-dioxepin];

11-(p.toluenesulfonyloxyethyl) 3-chloro [11H-dibenzo (b,e)-1,4-dioxepin];

N-pentamethylene [3-chloro 11H-dibenzo (b,e)-1,4-dioxepin-11-yl] ethylamine; and N-pentamethylene [3-chloro 11H-dibenzo (b,e)-1,4-dioxepin-11-yl] ethylamine fumarate.

EXAMPLE 4 dl N-diethyl 2-[8-chloro11H-dibenzo(b,e)-1,4-dioxepin-11-yl] ethylamine and its hydrochloride According to the procedure given in Example 1, starting from 2-(2-hydroxy-4-chloro) phenoxybenzoic acid, there were successively obtained:

8-chloro 11H-dibenzo (b,e)-1,4-dioxepin-11-one 11-(methoxycarbonylmethylidene)-8-chloro [11H-dibenzo (b,e)-1,4-dioxepin], Z and E isomers;

11-(methoxycarbonylmethyl)-8-chloro [11H-dibenzo (b,e)-1,4-dioxepin], which is an oily product;

11-hydroxyethyl-8-chloro [11H-dibenzo (b,e)-1,4-dioxepin];

11-(p.toluenesulfonyloxyethyl)-8-chloro [dibenzo (b,e)-1,4-dioxepin], M.P.: 90°–92° C.;

N-diethyl [8-chloro 11H-dibenzo (b,e)-1,4-dioxepin-11-yl] ethylamine; and

N-diethyl [8-chloro 11H-dibenzo (b,e)-1,4-dioxepin-11-yl] ethylamine hydrochloride, M.P.: 150°–154° C.

EXAMPLE 5

N-dimethyl 2-[2-trifluoromethyl 11H-dibenzo (b,e)-1,4-dioxepin-11-yl] ethylamine, and its fumarate 2-trifluoromethyl 11H-dibenzo (b,e)-1,4-dioxepin-11-one was obtained according to the following reactions:

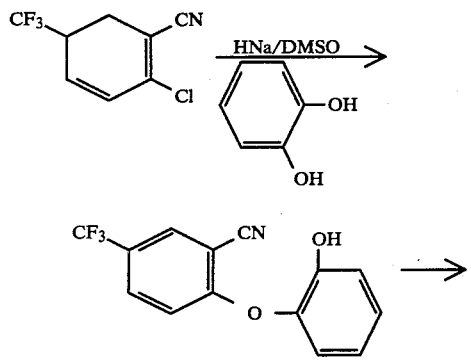

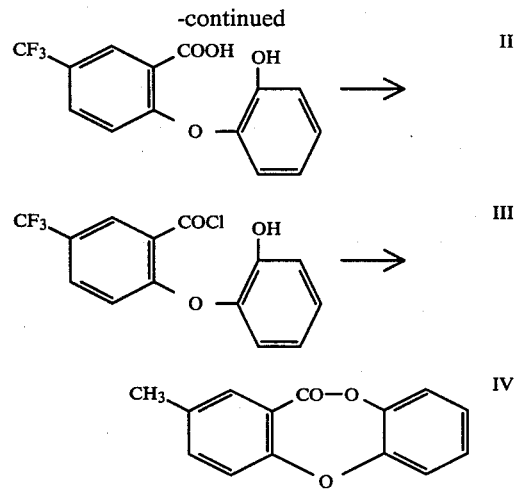

(I) In an inert atmosphere, there was prepared a solution of sodium monosalt of pyrocatechine in anhydrous dimethyl sulfoxide, starting from 1 mole of pyrocatechine and 0.5 mole of sodium hydride in 350 ml of anhydrous dimethylsulfoxide. To this solution, there was poured, for 7 hours, a solution of 0.5 mole of 2-chloro-5-trifluoromethyl benzonitrile in 300 ml of dimethyl sulfoxide. The mixture was then heated up to 60° C. and maintained at this temperature for 5 hours. The dimethyl sulfoxide was evaporated under vacuum. The residue was taken up with water and acidified. The product was extracted with ether. The solvent was evaporated and the residue was crystallized in cyclohexane/benzene 70/30. yield: 74.5 g, 53% M.P.: 115°–118° C.

(II) 83.7 g of the above nitrile were added to 315 ml of an aqueous solution at 40% of NaOH. The reactional mixture was refluxed for 4 hours and then diluted with ice, acidified and extracted with ether. The solvent was evaporated off and the oily residue 87 g. (yield: 97%) was used in the raw state for the following reaction.

(III) 96.6 g of the above acid in solution in 400 ml of dry benzene were treated with 154 g of thionyl chloride while refluxing for 4 hours. The excess of thionyl chloride and the excess of benzene were evaporated under vacuum. The oily residue (130 g) was used, without recrystallization, for the cyclization.

(IV) A solution of 130 g of the above acid chloride in 150 ml of benzene was poured, for 8 hours, in a solution of 131 g of triethylamine in 1500 ml of benzene at room temperature. The reactional mixture was left at room temperature for 15 hours, whereafter it was washed with one N solution of hydrochloric acid and, then with water. The organic solution was dried; then evaporated to dryness under vacuum. The oily residue, 93 g, was filtered on a gel of silica in methylene chloride.

The top fraction was evaporated and recrystallized in hexane: yield: 39.4 g of product M.P.: 55°–58° C. (M.K.).

2-trifluoromethyl 11-(methoxycarbonylmethylidene) 11 H-dibenzo (b,e)-1,4-dioxepin, oily product, B.P./0.01 mmHg. 150°–160° C.;

2-trifluoromethyl-11-(methoxycarbonylmethyl) [11 H-dibenzo (b,e)-1,4-dioxepin], raw oil;

2-trifluoromethyl-11-hydroxyethyl ]11 H-dibenzo (b,e)-1,4-dioxepin], raw oil;

2-trifluoromethyl-11-(p.toluenesulfonyloxyethyl) dibenzo (b,e)-1,4-dioxepin. M.P. 98°–102° C. (M.K.)

N-dimethyl 2-[2-trifluoromethyl 11 H-dibenzo (b,e)-1,4-dioxepin-11-yl] ethylamine; and
N-dimethyl 2-[2-trifluoromethyl 11 H-dibenzo (b,e)-1,4-dioxepin-11-yl] ethylamine fumarate. M.P. 170°–180° C. (M.K.).

EXAMPLE 6

N-diethyl-2-[7,8-dichloro 11 H-dibenzo (b,e)-1,4-dioxepin-11-yl] ethylamine

According to the procedure given in Example 1, starting from 2-(4,5-dichloro-2-phenoxy) benzoic acid, there were successively obtained:

7,8-dichloro 11 H-dibenzo (b,e)-1,4-dioxepin-11-one, M.P.: 141°–144° C.;
11-(methoxycarbonylmethylidene)-7,8-dichloro [11 H-dibenzo (b,e)-1,4-dioxepin], Z and E isomers;
11-(methoxycarbonylmethyl)-7,8-dichloro [11 H-dibenzo (b,e)-1,4-dioxepin];
11-hydroxyethyl-7,8-dichloro [11 H-dibenzo (b,e)-1,4-dioxepin]
11-(p.toluenesulfonyloxyethyl)-7,8-dichloro [11 H-dibenzo (b,e)-1,4-dioxepin];
N-diethyl [7,8-dichloro 11 H-dibenzo (b,e)-1,4-dioxepin-11-yl] ethylamine; and
N-diethyl [7,8-dichloro 11 H-dibenzo (b,e)-1,4-dioxepin-11-yl] ethylamine, hydrochloride.

EXAMPLE 7

N-diethyl 2-[11 H-dibenzo (b,e)-1,4-thioxepin-11-yl] ethylamine

According to the procedure given in Example 1, starting from 2-(2-hydroxyphenyl) thiobenzoic acid (M.P.: 178°–180° C.), there were successively obtained:

11 H-dibenzo (b,e)-1,4-thioxepin-11-one, B.P./0.005 mmHg: 160°–164° C., M.P.: 128°–130° C.;
11-(methoxycarbonylmethylidene) [11 H-dibenzo (b,e)-1,4-thioxepin]
  A isomer: M.P. : 126°–130° C. (acetonitrile)
  B isomer: M.P.: 108°–109° C. (isopropylic ether)
11-(methoxycarbonylmethyl) [11 H-dibenzo (b,e)-1,4-thioxepin] which is an oily product;
11-(p.toluenesulfonyloxyethyl) [11 H-dibenzo (b,e)-1,4-thioxepin] M.P.: 100°–104° C. (M.K.); and
N-diethyl 2-[11 H-dibenzo (b,e)-1,4-thioxepin-11-yl] ethylamine
N-diethyl 2-[11 H-dibenzo (b,e)-1,4-thioxepin-11-yl] ethylamine hydrochloride.

EXAMPLE 8 dl 4-methyl-1-{2-[11 H-dibenzo (b,e)-1,4-dioxepin-11-yl]ethyl} piperazine, and its difumarate Starting from p.toluenesulfonate prepared in Step E of Example 1 and 4-methylpiperazine, there was obtained dl 4-methyl-1-{2-[11 H-dibenzo (b,e)-1,4-dioxepin-11-yl] ethyl} piperazine, which is transformed in its difumarate M.P.: 205°–208° C. (water).

EXAMPLE 9

[11 H-dibenzo (b,e)-1,4-dioxepin-11-yl] propylamine

Step A

[11 H-dibenzo (b,e)-1,4-dioxepin-11-yl] propionitrile 13.2 g of p.toluenesulfonate prepared in Example 1 Step E, 100 ml of dimethylsulfoxide and 2.5 g of sodium cyanide were included in a closed reactor. The mixture was heated up to 90° C. and maintained at this temperature for one hour. The mixture was cooled down and then poured on to cracked ice and the precipitate was exhausted thrice with methylene chloride. The methylenic solutions were washed with water, dried, filtered off, and evaporated to dryness. There was so obtained a dry residue, weighing about 14 g, which contains a little dimethylsulfoxide. The raw product was stirred with 40 ml of water for 24 hours, then the crystals were separated out and dried under vacuum. There were isolated 7.7 g of pure product melting at 82°–86° C. Another crystallization from isopropylic ether gave a product melting at 82°–85° C. (yield: 91%).

Step B

3-[11 H-dibenzo (b,e)-1,4-dioxepin-11-yl] propylamine 0.6 g of sodium borohydride and 1.6 ml of tetrahydrofuran were introduced in a three-necked flask. A mixture of 1.82 g of trifluoroacetic acid and 1.6 ml of tetrahydrofuran was poured in, while cooling at about 0° C. This introduction lasted about 15 minutes, while a strong cooling was necessary. Then the cooling was stopped and the temperature of the mixture rose up to 15°–20° C. There was then added to this milky solution, for about 30 minutes, a solution of 4 g of [11 H-dibenzo (b,e)-1,4-dioxepin-11-yl] propionitrile in 6 ml of tetrahydrofuran. The mixture was stirred for one hour, then cooled down to 10° C. and 5 ml of water were added. The tetrahydrofuran was evaporated. The residue was taken up with a mixture of water and ether. The either phase was exhausted with an acid, then alkalized. The alkaline phase was exhausted with ether and evaporated to dryness. There were obtained 1.3 g of a raw product which is purified by transformation in hydrochloride M.P.: 188°–194° C.

EXAMPLE 10 dl 1-{2-[11 H-dibenzo (b,e)-1,4-dioxepin-11-yl] ethyl} pyrrolidine and its hydrochloride Step A

[11 H-dibenzo (b,e)-1,4-dioxepin-11-yl] methylidene carboxylic acid (Z and E isomers)

5.8 g of 11-(methoxycarbonyl methylidene) dibenzo (b,e)-1,4-dioxepin (B isomer) prepared in Example 1 step B were suspended in 130 ml of methanol, and 26 ml of a solution of sodium hydroxide at 40% were added to this suspension. The mixture was left at rest for 12 hours at room temperature, then methanol was eliminated under reduced pressure. The obtained clear solution was diluted with 50 ml of water then exhausted with ether. The ether phase was eliminated and the aqueous phase was acidified with concentrated hydrochloric acid, while cooling at 0° C. [11 H-dibenzo (b,e)-1,4-dioxepin-11-yl] methylidene carboxylic acid precipitated. It was collected, suctioned off, washed with water and dried under vacuum in a dessicator over phosphoric acid. There were obtained 5 g of a product melting at 174°–180° C., which recrystallized from hot ethyl acetate gives 1.6 g of a pure isomer melting at 185°–195° C. This product is quite soluble in a 0.1N solution of sodium hydroxide. According to the same procedure, starting from 6.7 g of 11-(methoxycarbonylmethylidene) 11 H-dibenzo (b,e)-1,4-dioxepin, A isomer, there were obtained 5.8 g of [11 H-dibenzo (b,e)-1,4-dioxepin-11-yl] methylidene carboxylic acid (A isomer), melting at 186°–190° C.

Step B 1.2 g of [11 H-dibenzo (b,e)-1,4-dioxepin-11-yl] methylidene carboxylic acid, 10 ml of acetone and 1 g of triethylamine were introduced in a three-necked flask. To this clear solution there were added 0.46 g of purified cyanuryl chloride (M.P.: 144°–145° C.). The reaction is exothermic so the internal temperature was maintained at about 15° C. with an ice-water bath. The disappearance of the cyanuryl chloride was controlled by chromatography, whereafter 0.35 g of pyrrolidine were then added. The reactants were left in contact for 95 minutes. The acetone solution was evaporated to dryness. The residue was taken up with methylene chloride. The methylene solution was successively washed with water, with a one N solution of hydrochloric acid, then with a one N solution of sodium hydroxide and finally with water. This solution was dried and then evaporated to dryness. There was obtained 1 g of pyrrolinidinic amide. The residue was purified by chromatography on a gel of silica and elution with a mixture of ethyl acetate/benzene. The middle fraction gave 0.5 g of pure product (M.P.: 134°–136° C.) which is recrystallized from acetonitrile to give a product melting at 145°–149° C.

Step C

1-[11 H-dibenzo (b,e)-1,4-dioxepin-11-yl] acetyl pyrrolidine 3.5 g of turnings of aluminium previously treated with hydrochloric acid, and 20 ml of ether, were suspended in a conical flask, then there were added 1.7 g of mercuric chloride. The addition of mercuric chloride provoked the reflux of the solvent and the formation of a precipitate. There were then added 6 g. of 1-[11 H-dibenzo (b,e)-1,4-dioxepin-11-yl] methylidene carbonyl pyrrolidine in solution in 30 ml of tetrahydrofuran while stirring, followed by a mixture of 8 ml of acetonitrile and 1.58 ml of water, over about 3 hours. After that time, the alumina which is formed was separated off and rinsed with some ml of tetrahydrofuran. The filtrates were collected together and evaporated to dryness. The dry residue weighed 5.4 g.

Step D

N-{2-[11 H-dibenzo (b,e)-1,4-dioxepin-11-yl] ethyl}pyrrolidine

The dry residue above obtained was dissolved in 45 ml of ethyl acetate. 0.5 g of palladium on charcoal (at 5% of Pd) were added and the catalytic hydrogenation was started. Thereafter, the mixture was purged with bubbling of nitrogen under a pressure 50 bars. When the absorption of hydrogen was achieved, the catalyst was separated off and rinsed several times with ethanol. The filtrates are collected together and acidified with gaseous hydrochloric acid. The hydrochloride precipitated out. The suspension was left at rest overnight in a refrigerator. Then the precipitate was filtered off. The crystals were dried and recrystallized from acetonitrile. dl 1-{2-[11 H-dibenzo (b,e)-1,4-dioxepin-11-yl] ethyl} pyrrolidine, hydrochloride melts at 191°–197° C. with decomposition.

The same product may be obtained starting from 11-p.toluenesulfonyloxyethyl) 11 H-dibenzo (b,e)-1,4-dioxepin refluxed with pyrrolidine in dimethyl formamide. The obtained base was then converted into the corresponding hydrochloride which crystallizes with 0.33 mole of water and melts at 195°–197° C.

EXAMPLE 11 dl N-diethyl-3-[11 H-dibenzo (b,e)-1,4-dioxepin-11-yl] propylamine and its citrate 2.5 g of [11 H-dibenzo (b,e)-1,4-dioxepin-11-yl] propylamine are dissolved in 40 ml of isopropylic ether and 0.90 g of acetaldehyde were added. The mixture was stirred for 4 hours at room temperature and there was added a solution of 1.04 g of potassium borohydride in 10 ml of methanol and 10 ml of water. The reactants were left in contact at 0° C. for one hour and then the excess of reactive product was destroyed by an addition of acetic acid. The mixture was then alkalized with a solution of sodium hydroxide. The orgianic phase was washed with water, under stirring, until the washing was neutral, then it was dried and evaporated to dryness.

The residue, which is N-diethyl 3-[11 H-dibenzo (b,e)-1,4-dioxepin-11-yl] propylamine is taken up with ethanol and treated with a solution of citric acid in ethanol to give the corresponding citrate. The crystals were collected and purified by recrystallization from ethanol.

N-diethyl 3-[11 H-dibenzo (b,e)-1,4-dioxepin-11-yl]propylamine is insoluble in water and ethanol and melts at 123°–127° C.

The compounds listed in the following table were prepared according to the procedures given in the above examples.

TABLE

| Ex. | R | R' | $R_1$ | $R_2$ | A | n | Salt | M.P. |
|---|---|---|---|---|---|---|---|---|
| 12 | H | H | $CH_3$ | $CH_3$ | | 0 | 2 | Fumarate 145–47° MK |
| 13 | H | H | H | $-CH\overset{\oplus}{\underset{CH_3}{\diagup C_2H_5}}$ | | 0 | 2 | Fumarate 146–77° MK |

TABLE-continued

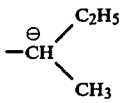

| Ex. | R | R' | R₁ | R₂ | A | n | Salt | M.P. |
|---|---|---|---|---|---|---|---|---|
| 14 | H | H | H | t Bu | 0 | 2 | Fumarate 236–39° MK |
| 15 | H | H | H | CH₃ | 0 | 2 | Fumarate 161–64° MK |
| 16 | H | H | H | isopropyl, i.e., —CH(CH₃)₂ | 0 | 2 | Fumarate 186–90° MK |
| 17 | H | H | CH₃ | CH₃ | S | 2 | Hydrochloride 205–15° MK |
| 18 | H | Cl—7,8 | CH₃ | CH₃ | 0 | 2 | Hydrochloride 206–10° MK |
| 19 | H | H | H | —CH(C₂H₅)(CH₃) | 0 | 2 | Fumarate 170–80° MK |
| 20 | H | Cl—7,8 | —(CH₂)₄— | | 0 | 2 | Hydrochloride 192–95° MK |
| 21 | H | CH₃—8 | CH₃ | CH₃ | 0 | 2 | Fumarate 128–33° MK |
| 22 | Cl—2 | H | CH₃ | CH₃ | 0 | 2 | Fumarate 156–60° MK |
| 23 | Cl—2 | H | —(CH₂)₄— | | 0 | 2 | Fumarate 182–87° MK |
| 24 | H | H | —(CH₂)₅— | | S | 2 | Hydrochloride 200–8° MK |
| 25 | H | CH₃—7 | CH₃ | CH₃ | 0 | 2 | Fumarate 176–81° MK |
| 26 | H | H | —(CH₂)₄— | | S | 2 | Hydrochloride 190–96° MK |
| 27 | H | Cl—7 | C₂H₅ | C₂H₅ | 0 | 2 | Hydrochloride 135–40° MK |
| 28 | H | Cl—7 | 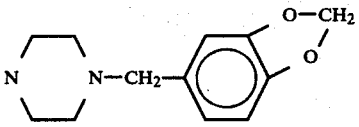 | | 0 | 2 | dihydrochloride 225–35° MK |
| 29 | H | H | CH₃ | CH₃ | 0 | 3 | Fumarate 66–70° MK |

Pharmacological study of compounds of the invention

1. Anticonvulsant activity

This activity was evidenced in mice. Doses of 1.5–10 mg/kg of the compounds administered intraperitoneally protect the animals against convulsions provoked by electric shock, decreasing by 50% the number of convulsions.

2. Inhibition of aggressivity

The aggressivity inhibiting activity was tested in isolated rats and mice after removal of the bulbus olfactorius (L. Valzelli: Aggressive behaviour, 1969, p. 70–76, Excerpta Medical Foundation, Amsterdam). Doses of 10 and 20 mg/kg administered intraperitoneally, decrease by 35 to 80% the number of aggressive or killing animals. No side effect such as hyperactivity or depression, is observed.

3. Antagonizing effect of Tetrabenazine

The compounds of the invention, when administered subcutaneously at the dose of 10 to 25 mg/kg in mice, inhibit the eyelid ptosis provoked by the injection of tetrabenazine. This inhibition is complete for most of the compounds and this activity is at least twice as high as that observed for Mianserin. ®

4. Potentialization of amphetamine

The intraperitoneal injection of 5 mg/kg of amphetamine in rats provokes stereotypical movements. When administered orally at the dose of 10 to 25 mg/kg 3 hours before the amphetamine, the compounds of the invention potentialize the beginning and the duration of the movements at a similar degree as Imipramine.

5. Antagonism of hypothermia

The compounds of the invention injected intraperitoneally or subcutaneously at the dose of 0.1 to 25 mg/kg in mice antagonize the hypothermia appearing after injection of 2.5 mg reserpin S.C. or 15 mg/kg S.C. of apomorphine.

6. Anticatatonic activity

When administered intraperitoneally at doses of 20–40 mg/kg in rats, the compounds of the invention inhibit the catatonia provoked by Temantil. ® This inhibition is as effective as that obtained by amitryptiline.

7. Toxicity

The compounds of the invention are administered I.P. in increasing doses to groups of mice. The medium lethal dose is calculated graphically by the method of Tainter and Miller. This dose was found to be situated between 80 and 100 mg/kg. By oral route the LD₅₀ is of 250 to 500 mg/kg in mice and >500 mg/kg in rats.

What we claim is:

1. A compound selected from the group consisting of a substituted 11 H-dibenzooxepine of formula I:

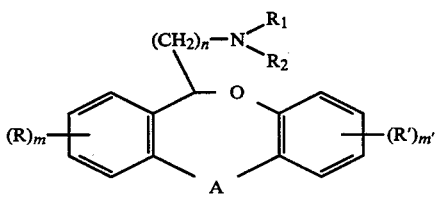

wherein
R and R', the same or different, are hydrogen, halogen, lower-alkyl, lower-alkoxy, trifluoromethyl, trifluoromethoxy, trifluoromethylthio, lower-alkylenedioxy, or lower-alkylthio, A represents oxygen or sulphur, $R_1$ and $R_2$, the same or different, represent hydrogen, lower-alkyl, or lower-hydroxyalkyl, n represents an integer of 2 to 4, inclusive, m and m', the same or different, are the integers 1 or 2, lower-alkyl, lower-alkoxy, lower-hydroxyalkyl, lower-alkylenedioxy, and lower-alkylthio, as used in the foregoing, having in each case one to five carbon atoms, inclusive, an acid addition salt thereof with a therapeutically-compatible mineral or organic acid, and an optical isomer thereof.

2. An acid addition salt of a compound of claim 1 with a therapeutically-compatible mineral or organic acid.

3. An optical isomer of a compound as claimed in claim 1 or claim 2.

4. Compound of claim 1 which is selected from the group consisting of dl N-diethyl 2-[11 H-dibenzo (b,e)-1,4-dioxepin-11-yl] ethylamine, an acid addition salt thereof, and an optical isomer thereof.

5. Compound of claim 1 which is selected from the group consisting of dl N-dimethyl 2-[11 H-dibenzo (b,e)-1,4-dioxepin-11-yl] ethylamine, an acid addition salt thereof, and an optical isomer thereof.

6. Compound of claim 1 which is selected from the group consisting of dl N-diethyl 2-[2-chloro 11 H-dibenzo (b,e)-1,4-dioxepin-11-yl] ethlyamine, an acid addition salt thereof, and an optical isomer thereof.

7. Compound of claim 1 which is selected from the group consisting of dl 3-[11 H-dibenzo (b,e)-1,4-dioxepin-11-yl] propylamine, an acid addition salt thereof, and an optical isomer thereof.

8. Compound of claim 1 which is selected from the group consisting of dl N-diethyl 3-[11 H-dibenzo (b,e)-1,4-dioxepin-11-yl] propylamine, an acid addition salt thereof, and an optical isomer thereof.

9. Compound of claim 1 which is selected from the group consisting of dl N-diethyl 2-[3-chloro 11 H-dibenzo (b,e)-1,4-dioxepin-11-yl] ethylamine, an acid addition salt thereof, and an optical isomer thereof.

10. Compound of claim 1 which is selected from the group consisting of dl N-diethyl 2-[8-chloro 11 H-dibenzo (b,e)-1,4-dioxepin-11-yl] ethylamine, an acid addition salt thereof, and an optical isomer thereof.

11. Compound of claim 1 which is selected from the group consisting of dl N-sec butyl 2-[11 H-dibenzo (b,e)-1,4-dioxepin-11-yl] ethylamine, an acid addition salt thereof, and an optical isomer thereof.

12. Compound of claim 1 which is selected from the group consisting of dl N-terbutyl 2-[11 H-dibenzo (b,e)-1,4-dioxepin-11-yl] ethylamine, an acid addition salt thereof, and an optical isomer thereof.

13. Compound of claim 1 which is selected from the group consisting of dl N-methyl 2-[11 H-dibenzo (b,e)-1,4-dioxepin-11-yl] ethylamine, an acid addition salt thereof, and an optical isomer thereof.

14. Compound of claim 1 which is selected from the group consisting of dl N-isopropyl 2-[11 H-dibenzo (b,e)-1,4-dioxepin-11-yl] ethylamine, an acid addition salt thereof, and an optical isomer thereof.

15. Compound of claim 1 which is selected from the group consisting of dl N-diethyl 2-[7,8-dichloro 11 H-dibenzo (b,e)-1,4-dioxepin-11-yl] ethylamine, an acid addition salt thereof, and an optical isomer thereof.

16. Compound of claim 1 which is selected from the group consisting of dl N-dimethyl 2-[2-trifluoromethyl 11 H-dibenzo (b,e)-1,4-dioxepin-11-yl] ethylamine, an acid addition salt thereof, and an optical isomer thereof.

17. Compound of claim 1 which is selected from the group consisting of dl N-diethyl 2-[11 H-dibenzo (b,e)-1,4-thioxepin-11-yl] ethylamine, an acid addition salt thereof, and an optical isomer thereof.

18. A pharmaceutical composition comprising as active ingredient at least one compound as claimed in claim 1 or an acid addition salt thereof in conjunction with an inert, non-toxic pharmaceutically-acceptable carrier.

19. A pharmaceutical composition as claimed in claim 18 wherein the active ingredient is present at a dosage of 0.5 to 10 mg.

20. A pharmaceutical composition as claimed in claim 18 which is in a pharmaceutical form adapted to administration by oral, rectal, parenteral, or sublingual route.

21. A method of treating central nervous system disorders in mammals, which comprises administering to a patient suffering from such condition a therapeutically effective amount of a compound of claim 1 or a pharmaceutical composition as claimed in claim 18, claim 19, or claim 20.

22. A compound of claim 1 which is selected from the group consisting of dl N-dimethyl 2-[11 H-dibenzo (b,e)-1,4-thioxepin-11-yl] ethylamine, an acid addition salt thereof, or an optical isomer thereof.

* * * * *